(12) United States Patent  (10) Patent No.: US 7,569,821 B2
Ohashi  (45) Date of Patent: Aug. 4, 2009

(54) BIOLOGICAL INFORMATION MEASURING APPARATUS

(75) Inventor: Mitsuo Ohashi, Yokohama (JP)

(73) Assignee: Spectratech Inc., Tokyo (JP)

( * ) Notice: Subject to any disclaimer, the term of this patent is extended or adjusted under 35 U.S.C. 154(b) by 0 days.

(21) Appl. No.: 12/255,234

(22) Filed: Oct. 21, 2008

(65) Prior Publication Data

US 2009/0108204 A1    Apr. 30, 2009

(30) Foreign Application Priority Data

Oct. 25, 2007    (JP) ............................. 2007-277513

(51) Int. Cl.
*G01J 5/02*    (2006.01)
(52) U.S. Cl. ..................... 250/339.06; 250/339.01; 250/343
(58) Field of Classification Search ............ 250/338.1, 250/338.5, 339.01, 339.06, 343; 382/128
See application file for complete search history.

(56) References Cited

U.S. PATENT DOCUMENTS

2005/0249667 A1* 11/2005 Tuszynski et al. ............ 424/9.3

2006/0222224 A1* 10/2006 Ohashi ..................... 382/128

FOREIGN PATENT DOCUMENTS

| JP | 3623734 B2 | 12/2004 |
| JP | 4097522 B2 | 3/2008 |
| WO | 02/32317 A1 | 4/2002 |

* cited by examiner

*Primary Examiner*—David P Porta
*Assistant Examiner*—Mark R Gaworecki
(74) *Attorney, Agent, or Firm*—Rossi, Kimms & McDowell, LLP

(57) ABSTRACT

A light emission section spread-spectrum modulates a base band signal at a chip frequency f to thereby generate a primary modulated signal, modulates the primary modulated signal at a frequency 2f to thereby generate a secondary modulated signal, and emits a near-infrared light beam having a specific wavelength into a living organism on the basis of the secondary modulated signal. A light detection section receives a reflected light beam from the interior of the living organism in an effective detection band 2f, converts it to an electrical detection signal, and converts the detection signal to a digital signal at a sampling frequency 4f. The light detection section then demodulates the digital signal at the frequency 2f to thereby generate a primary demodulated signal, and demodulates the primary demodulated signal through spectrum despreading to thereby generate a secondary demodulated signal. Thus, a biological information signal representing biological information is output.

8 Claims, 12 Drawing Sheets

FIG.10

WHEN SPREADING FACTOR IS "1"

$$C_{ch,1,0} = 1$$

WHEN SPREADING FACTOR IS "2"

$$\begin{pmatrix} C_{ch,2,0} \\ C_{ch,2,1} \end{pmatrix} = \begin{pmatrix} C_{ch,1,0} & C_{ch,1,0} \\ C_{ch,1,0} & -C_{ch,1,0} \end{pmatrix} = \begin{pmatrix} 1 & 1 \\ 1 & -1 \end{pmatrix}$$

WHEN SPREADING FACTOR IS "$2^{(n+1)}$"

$$\begin{pmatrix} C_{ch,2^{(n+1)},0} \\ C_{ch,2^{(n+1)},1} \\ C_{ch,2^{(n+1)},2} \\ C_{ch,2^{(n+1)},3} \\ \vdots \\ C_{ch,2^{(n+1)},2^{(n+1)}-2} \\ C_{ch,2^{(n+1)},2^{(n+1)}-1} \end{pmatrix} = \begin{pmatrix} C_{ch,2^n,0} & C_{ch,2^n,0} \\ C_{ch,2^n,0} & -C_{ch,2^n,0} \\ C_{ch,2^n,1} & C_{ch,2^n,1} \\ C_{ch,2^n,1} & -C_{ch,2^n,1} \\ \vdots & \vdots \\ C_{ch,2^n,2^n-1} & C_{ch,2^n,2^n-1} \\ C_{ch,2^n,2^n-1} & -C_{ch,2^n,2^n-1} \end{pmatrix}$$

BIOLOGICAL INFORMATION MEASURING APPARATUS

BACKGROUND OF THE INVENTION

1. Field of the Invention

The present invention relates to a biological information measuring apparatus for acquiring various types of biological information associated with the metabolism of a living organism, such as biological density, water content, blood oxygen level, oxygen saturation, glucose level, blood glucose level, and pulse, on the basis of a phenomenon that propagation of light through the living organism changes differently depending on the wavelength of the propagating light.

2. Background Art

In recent years, there have been actively proposed, as an apparatus and method for conveniently analyzing the interior of a living organism in a noninvasive manner, apparatuses and methods for acquiring information on the interior of a living organism by emitting light from a light source provided on the surface of the living organism to the interior of the organism, and receiving reflected light which has propagated through the living organism while being scattered and absorbed therein, and which has reached the living organism surface. For example, in Japanese Patent No. 3623743, the applicant of the present application has proposed a biological information measuring apparatus which measures biological information by making use of spread-spectrum modulation and demodulation. This biological information measuring apparatus can acquire information, for example, at the cerebral cortical layer through measurement of oxygen level in blood on the basis of a change in absorption of near-infrared light by hemoglobin.

In the apparatus disclosed in Japanese Patent No. 3623743, a light emitting section is configured to spread-spectrum modulate a signal to be transmitted (a base band signal) and emit light from a semiconductor laser. As is known, the power spectrum of a spread-spectrum modulated signal is generally represented as shown in FIG. 12. Thus, light output on the basis of a signal having a power spectrum as shown in FIG. 12 has a large output (intensity) at direct current (DC) and frequencies in the vicinity of DC. When information of a living organism is measured by use of light having such a power spectrum, the measurement is likely to be affected by DC component variations (e.g., drift variation, offset variation, and 1/f noise) of a light source driver, a light source, an optical detector, and an amplifier; i.e., so-called DC problems associated with spectrum spreading, so that, although relative measurement is possible, strict measurement may be difficult.

Further, in the apparatus disclosed in Japanese Patent No. 3623743, a light detection section is configured to convert light having propagated through a living organism to an electrical detection signal (analog signal), and convert the detection signal (analog signal) to a digital signal by means of an AD converter. However, this patent does not clearly show a sampling frequency at which the AD converter converts an analog signal to a digital signal. For example, in the case where the conversion processing is performed at a sampling frequency corresponding to the emission period of light, a detection signal (analog signal) corresponding to received light cannot be sampled over the entire signal band (frequencies) thereof, so that the detection signal (analog signal) may fail to be properly reproduced in the form of a digital signal. That is, the conventionally practiced measurement of the interior of a living organism by making use of spectrum spreading cannot be said to effectively use frequencies necessary for emission of light, detection of light, conversion of detected light to an electrical signal, etc. Accordingly, the conventional apparatus may fail to properly and reliably obtain information regarding a living organism, which information is carried by light having propagated through the living organism.

SUMMARY OF THE INVENTION

The present invention has been accomplished in order to solve the aforementioned problems. An object of the present invention is to provide a biological information measuring apparatus which solves the DC problems associated with spectrum spreading and improves the efficiency of use of frequencies associated with measurement, and which enables noninvasive measurement of biological information associated with the metabolism of a living organism.

The present invention provides a biological information measuring apparatus is composed of a light emission section and a light detection section.

The light emission section comprises:

base-band-signal output means for generating and outputting a predetermined base band signal;

spread-code-sequence generation means for generating a spread code sequence at a first frequency, the spread code sequence being used for modulating the base band signal through spread spectrum modulation;

first modulation means for spectrum-spreading the base band signal by using the spread code sequence generated by the spread-code-sequence generation means, to thereby output a primary modulated signal;

second modulation means for modulating the primary modulated signal output from the first modulation means by using a clock signal of a second frequency two times the first frequency, to thereby output a secondary modulated signal; and light generation means having at least one light source and emitting an near-infrared light beam into a living organism, the near-infrared light beam being generated on the basis of the secondary modulated signal output from the second modulation means and having a specific wavelength.

The light detection section comprises:

light receiving means for receiving the near-infrared light beam having been emitted from the light emission section and propagated through the living organism, converting the received near-infrared light beam to an electrical detection signal, and outputting the electrical detection signal;

signal component removal means for removing from the electrical detection signal a DC component, signal components of frequencies near DC, and signal components of frequencies equal to or higher than the second frequency, and outputting the electrical detection signal;

signal conversion means for converting the electrical detection signal output from the signal component removal means to a digital signal by using a clock signal of a third frequency two times the second frequency, the clock signal of the third frequency being supplied in consideration of a delay of the near-infrared light beam produced due to propagation of the near-infrared light beam through the living organism;

first demodulation means for demodulating the digital signal by using the clock signal of the second frequency, to thereby output a primary demodulated signal, the clock signal of the second frequency being supplied in consideration of the delay of the near-infrared light beam produced due to propagation of the near-infrared light beam through the living organism;

second demodulation means for spectrum-despreading the primary demodulated signal by using the spread code sequence to thereby output a secondary demodulated signal, the spread code sequence being supplied in consideration of the delay of the near-infrared light beam produced due to propagation of the near-infrared light beam through the living organism; and biological-information-signal output means for outputting a biological information signal representing biological information associated with the metabolism of the living organism by using the secondary demodulated signal output from the second demodulation means.

Preferably, the second frequency coincides with a width of an effective detection band in which the light receiving means of the light detection section can effectively detect the near-infrared light beam having propagated through the living organism.

Preferably, the base-band-signal output means of the light emission section generates and outputs a DC signal.

Preferably, the base-band-signal output means of the light emission section generates and outputs a generally pulse-shaped signal at an arbitrary frequency equal to or less than half the first frequency, and the light detection section further comprises third demodulation means for demodulating the second demodulated signal output from the second demodulation means by using the generally pulse-shaped signal supplied in consideration of the delay of the near-infrared light beam produced due to propagation of the near-infrared light beam through the living organism. In this case, preferably, the light emission section further comprises an error-correction-code addition means for adding an error correction code to the generally pulse-shaped signal output from the base-band-signal output means; and the light detection section further comprises error check means for checking consistency of the secondary demodulated signal by using the error correction code contained in the secondary demodulated signal output from the second demodulation means, and interpolation means for restoring the secondary demodulated signal through interpolation when the error check means determines that the secondary demodulated signal contains an error.

The biological information measuring apparatus of the present invention operates as follows. In the light emission section, the base-band-signal output means outputs a base band signal (e.g., a DC signal or a pulse-shaped signal) to the first modulation means. Further, the spread-code-sequence generation means outputs to the first modulation means a spread code sequence generated at a first frequency (i.e., the chip rate in spectrum spreading). Thus, the first modulation means modulates the output base band signal through spectrum spreading, and outputs a resultant primary modulated signal to the second modulation means. The second modulation means modulates the output primary modulated signal by using a clock signal of a second frequency two times the first frequency, and outputs a resultant secondary modulated signal to the light generation means. Thus, the light generation means emits an near-infrared light beam into a living organism, the near-infrared light beam being generated on the basis of the secondary modulated signal and having a specific wavelength.

Since the second modulation means produces the secondary modulated signal at the second frequency two times the first frequency, the secondary modulated signal can have a power spectrum in which the center of the main lobe is located at the first frequency and the main lobe extends from the frequency of DC to the second frequency. As a result, the output (strength) of the near-infrared light beam emitted by the light generation means becomes very small at DC, at frequencies near DC, and at the second frequency. Accordingly, through use of the near-infrared light beam emitted from the light emission section, the DC problems associated with spectrum spreading can be avoided efficiently.

Meanwhile, in the light detection section, the light receiving means receives the near-infrared light beam having the above-described power spectrum and having propagated through the living organism, converts the received near-infrared light beam to an electrical detection signal (analog signal), and outputs the electrical detection signal. The signal component removal means removes from the output electrical detection signal (analog signal) a DC component, signal components of frequencies near DC, and signal components of frequencies equal to or higher than the second frequency, and outputs the electrical detection signal to the signal conversion means.

In this case, according to the power spectrum of the above-described secondary modulated signal (i.e., the emitted near-infrared light beam), the near-infrared light beam received by the light receiving means also has a power spectrum in which the center of the main lobe is located at the first frequency and the main lobe extends from the frequency of DC to the second frequency. As a result, the strength of the electrical detection signal (analog signal) output from the light receiving means becomes very small at DC, at frequencies near DC, and at the second frequency. Accordingly, even when these signal components are removed, the electrical detection signal (analog signal) can satisfactorily maintain information necessary for measurement.

Further, the band width of the electrical detection signal (analog signal), from which the DC component, the signal components of frequencies near DC, and the signal components of frequencies equal to or higher than the second frequency have been removed by the signal component removal means, coincides with the effective detection band width of the light receiving means; i.e., the second frequency. As a result, the effective detection band width of the light receiving means can be utilized considerably efficiently.

The signal conversion means then converts the electrical detection signal (analog signal) output from the signal component removal mean to a digital signal by using a delayed clock signal of the third frequency (i.e., a sampling frequency) two times the second frequency. In other words, the signal conversion means converts the analog signal to a digital signal at a sampling frequency two times the effective detection band width of the light receiving means. Since the analog signal is converted to a digital signal at a sampling frequency two times the width of the effect detection band of the light receiving means; i.e., the signal band of the analog signal, information carried by the analog signal corresponding to the entirety of the effective detection band width of the light receiving means can be reproduced in the form of a digital signal very well. Thus, the efficiency of use of frequencies in spectrum spreading can be greatly improved.

The first demodulation means demodulates the detection signal (digital signal) by using the clock signal of the second frequency, to thereby output a primary demodulated signal. The primary demodulated signal is demodulated by the second demodulation means through spectrum dispreading, whereby the secondary demodulated signal is output. The biological-information-signal output means then outputs a biological information signal representing biological information by using the secondary demodulated signal. Accordingly, the influence of the DC problems associated with spectrum spreading can be eliminated, and the efficiency of use of frequencies required for emission and detection of near-infrared light and conversion of the detected near-infrared light to an electrical detection signal can be improved. Accordingly, the accuracy of obtained biological information can also be improved greatly. Notably, examples of biological information obtained from the biological information signal include biological density, water content, blood oxygen level, oxygen saturation, glucose level, blood glucose level, and pulse.

In the case where a generally pulse-shaped signal is output as the base band signal, an error correction code may be added to the pulse-shaped signal, on the basis of which a near-infrared light beam is emitted, to thereby enable output of a biological information signal. By virtue of this configuration, a more accurate biological information signal can be obtained, whereby considerably accurate biological information can be obtained.

According to another aspect of the present invention, the spread-code-sequence generation means of the light emission section changes the spreading factor of the spread code sequence in accordance with the intensity of the near-infrared light beam having propagated through the living organism and received by the light receiving means of the light detection section.

In this case, preferably, the spread-code-sequence generation means generates the spread code sequence with an increased spreading factor when the intensity of the near-infrared light beam having propagated through the living organism and received by the light receiving means of the light detection section is low and the SN ratio of the near-infrared light beam is low, and generates the spread code sequence with a decreased spreading factor when the intensity is high and the SN ratio is high. In this case, preferably, the spread-code-sequence generation means generates, as the spread code sequence, an orthogonal variable spreading factor code which guarantees the orthogonality between spread code sequences which differ in spreading factor.

By virtue of these configuration, when the intensity of the near-infrared light beam received by the light receiving means of the light detection section is low and the SN ratio of the near-infrared light beam is low due to influence of absorption and scattering within the living organism, the spread-code-sequence generation means can generate the spread code sequence with an increased spreading factor. Meanwhile, when the intensity of the near-infrared light beam received by the light receiving means of the light detection section is high and the SN ratio of the near-infrared light beam is high, the spread-code-sequence generation means can generate the spread code sequence with a decreased spreading factor.

In spectrum spreading, when the spreading factor increases, the SN ratio of a signal obtained through spectrum dispreading increases although the signal bandwidth of the signal becomes narrower; and when the spreading factor decreases, the signal bandwidth of the signal obtained through spectrum dispreading becomes wider although the SN ratio of the signal decreases. In view of this fact, when the intensity of the near-infrared light beam received by the light receiving means is low, the spreading factor is increased, whereby the SN ratio of the biological information signal corresponding to the near-infrared light beam having propagated through the living organism can be improved, although the signal bandwidth of the biological information signal decreases. Further, when the intensity of the near-infrared light beam received by the light receiving means is high, the spreading factor is decreased, whereby the signal bandwidth of the biological information signal corresponding to the near-infrared light beam having propagated through the living organism can be increased, although the SN ratio of the biological information signal slightly decreases.

In this case, the spread-code-sequence generation means can generate an orthogonal variable spreading factor (OVSF) sequence as the spread code sequence. By virtue of this configuration, the orthogonality between generated spread code sequences is guaranteed even when they differ in spreading factor. Therefore, even in the case where a region in which light intensity is weak is located adjacent to a region in which light intensity is strong, it is possible to prevent mutual interference of near-infrared light beams propagating through these regions. Accordingly, near-infrared light beams spread-spectrum modulated at different spreading factors can be emitted simultaneously, and, as a result, corresponding secondary demodulated signals can be produced satisfactorily and accurate biological information signals can be output.

BRIEF DESCRIPTION OF THE DRAWINGS

Various other objects, features, and many of the attendant advantages of the present invention will be readily appreciated as the same becomes better understood with reference to the following detailed description of the preferred embodiments when considered in connection with the accompanying drawings, in which:

FIG. 10 relates to a third embodiment of the present invention and is used for describing an orthogonal variable spreading factor code;

DETAILED DESCRIPTION OF PREFERRED EMBODIMENTS a. First Embodiment

Figure 1:
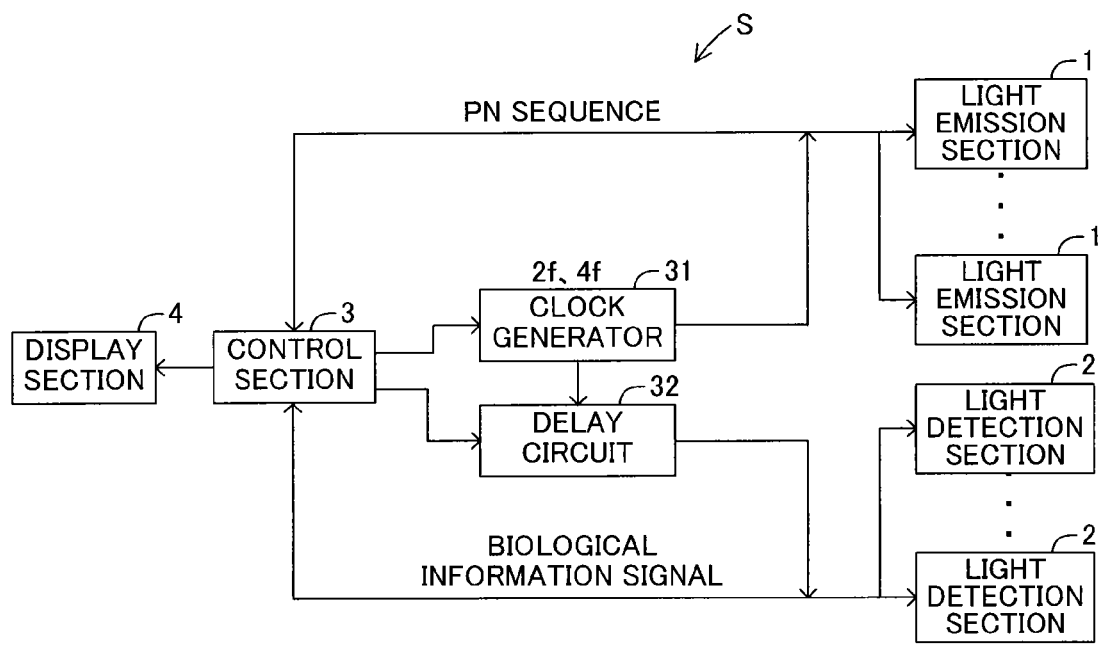
FIG. 1 is a block diagram schematically showing a biological information measuring apparatus according to a first embodiment of the present invention.

A first embodiment of the present invention will next be described with reference to the drawings. FIG. 1 is a block diagram schematically showing the configuration of a biological information measuring apparatus S according to the present invention. As shown in FIG. 1, the biological information measuring apparatus S includes a plurality of light emission sections 1 which emit light beams having specific wavelengths; and a plurality of light detection sections 2 which detect the light beams which have been emitted from the light emission sections 1 and propagated through a living organism while being reflected therein.

The light emission sections 1 and the light detection sections 2 are connected to a control section 3. The control section 3 includes, as a main component, a microcomputer including a CPU, ROM, RAM, a timer, etc., and totally controls the operation of the biological information measuring apparatus S. The control section 3 calculates, for example, a blood oxygen level in the brain, as biological information associated with the metabolism of a living organism, on the basis of the intensities of light beams detected by the light detection sections 2; more specifically, the intensities of light beams emitted from the light emission sections 1, which have been attenuated through propagation through the living organism.

The control section 3 includes a clock generator 31 and a delay circuit 32. The clock generator 31 supplies to the light emission sections 1 and the light detection sections 2 a clock signal having a frequency 2f (second frequency) which is equal to the width of an effective detection band of a light receiver 22 to be described later, which partially constitutes each light detection section 2 (hereinafter the clock signal having the frequency 2f will be referred to as the "clock signal of frequency 2f"), and a clock signal having a frequency 4f, which is two times the frequency 2f (hereinafter the clock signal having the frequency 4f will be referred to as the "clock signal of frequency 4f"). Notably, in the present specification, a frequency f is a first frequency, which can be freely set. The delay circuit 32 properly delays a PN sequence generated by each spread code sequence generator 11 (which will described later) of the light emission section 1 and supplied to the corresponding light detection section 2, and the clock signal of frequency 4f and the clock signal of frequency 2f supplied from the clock generator 31 to the light detection sections 2. Notably, since paths along which light beams propagate from the light emission sections 1 toward the light detection sections 2 may have different delay characteristics, the delay circuit 32 may be individually provided for each of the light detection sections 2 so as to obtain biological information more accurately.

The control section 3 outputs data representing the thus-calculated biological information to a display section 4. The display section 4 is formed of, for example, a liquid crystal display, and displays the biological information in a predetermined mode on the basis of the data supplied from the control section 3.

Figure 2:
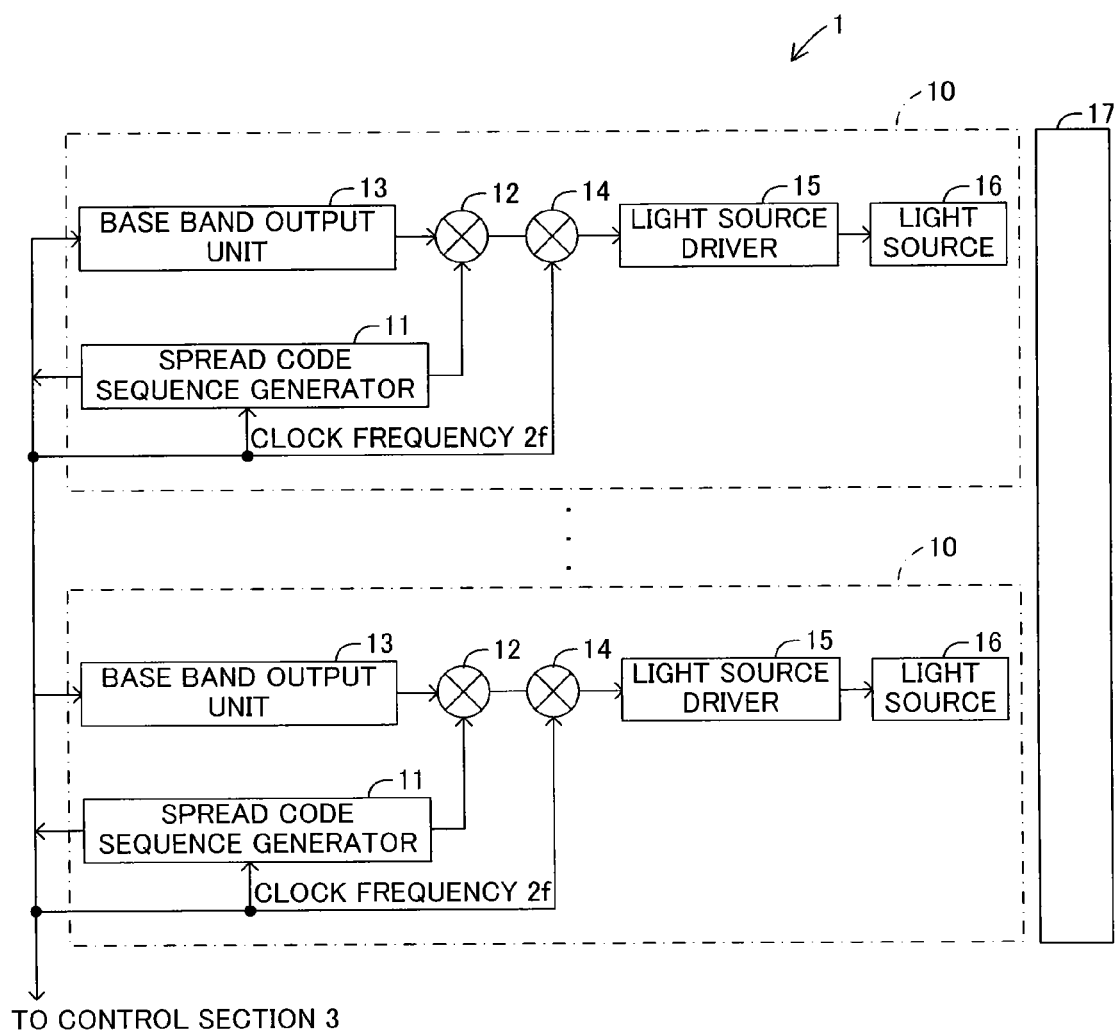
FIG. 2 is a block diagram schematically showing the configuration of a light emission section of FIG. 1.

The light emission sections 1 will next be described in detail. As shown in a block diagram of FIG. 2, each of the light emission sections 1 is formed of a plurality of light generation units 10 which generate light beams having different specific wavelengths. In the present embodiment, each light emission section 1 is formed of six light generation units 10. However, the number of the light generation units 10 is not limited thereto.

Each of the light generation units 10 emits a light beam having a specific wavelength on the basis of a spread-spectrum-modulated signal. Therefore, each of the light generation units 10 includes a spread code sequence generator 11 for generating a spread code sequence such as a 65536-bit pseudorandom noise (PN) sequence which consists of "+1" and "−1." The spread code sequence generator 11 generates, for example, a Hadamard sequence, an M sequence, or a Gold code sequence as a PN sequence.

The aforementioned Hadamard sequence, M sequence, and Gold code sequence are similar to those employed for spread spectrum modulation, and thus detailed description of their generation methods is omitted. However, these sequences will next be described briefly. The Hadamard sequence is obtained from each of the rows or columns of a Hadamard matrix which consists of "+1" and "−1." The M sequence is a binary sequence obtained by use of a shift register consisting of n 1-bit register units, each memorizing "0" or "+1." The shift register is configured such that the exclusive logical sum of the value of an intermediate register unit and the value of the final register unit is fed to the first register unit. Notably, in order to transform this binary sequence into a PN sequence, the value "0" is converted into "−1" through level conversion. The Gold code sequence is basically obtained through addition of two types of M sequences. Therefore, the Gold code sequence can increase the number of sequences considerably, as compared with the case of the M sequence. Among these sequences serving as PN sequences, two arbitrary sequences are orthogonal with each other, and the sum of products of the two sequences yields the value "0." That is, one of these sequences has zero correlation with the other sequences.

The spread code sequence generator 11 receives the clock signal of frequency 2f supplied from the clock generator 31. On the basis of the received clock signal of frequency 2f, the spread code sequence generator 11 generates a PN sequence such that the generation frequency of the PN sequence; i.e., a chip rate corresponding to the minimum generation interval of the PN sequence becomes equal to or less than f.

The PN sequence generated by the spread code sequence generator 11 is output to the control section 3, and is also output to a first multiplier 12. The first multiplier 12 computes the product of a DC signal output from a base band output unit 13 and the PN sequence supplied from the spread code sequence generator 11 to thereby spread-spectrum modulate the DC signal. In the following description, this spread-spectrum modulated DC signal will also be referred to as "primary modulated signal."

The primary modulated signal is output to a second multiplier 14. The second multiplier 14 receives the clock signal of frequency 2f supplied from the clock generator 31, as well as the primary modulated signal. The second multiplier 14 modulates the received primary modulated signal by the clock signal of frequency 2f. In the following description, this modulated primary modulated signal will also be referred to as the "secondary modulated signal."

Figure 3:
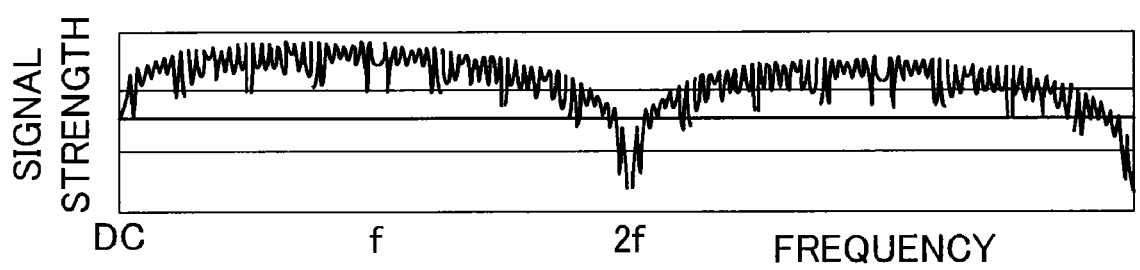
FIG. 3 is a graph showing the power spectrum of a spectrum-spread signal after being modulated by a second multiplier of FIG. 2.
Figure 12:
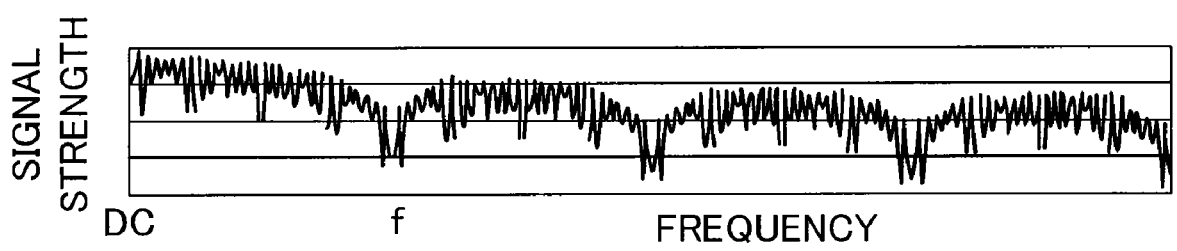
FIG. 12 is a graph showing the power spectrum of a typical spectrum-spread signal.

The primary modulated signal and the secondary modulated signal will now be described. As described above, the primary modulated signal is a signal obtained by spectrum modulating the DC signal, which serves as a base band signal, by use of the PN sequence supplied from the spread code sequence generator 11 and having a chip rate f. Therefore, the primary modulated signal typically has a power spectrum as shown in FIG. 12 in its frequency band. That is, as shown in FIG. 12, the primary modulated signal has a power spectrum such that it has strong signal components at direct current (DC) and frequencies near DC, and its signal strength decreases at the frequency f (chip rate f). In contrast, the secondary modulated signal is obtained by further modulating the primary modulated signal by the clock signal of frequency 2f; that is, at a clock frequency which is two times the chip rate f. Therefore, as shown in FIG. 3, the secondary modulated signal has a power spectrum which has a main lobe of frequency 2f whose center is the frequency f. Thus, in the case of the secondary modulated signal, the signal strength becomes the maximum at the frequency f, becomes very small at DC and frequencies near DC, and becomes very small at the frequency 2f.

The secondary modulated signal output from the second multiplier 14 is supplied to a light source driver 15. The light source driver 15 drives a light source 16 on the basis of the secondary modulated signal. The light source 16 is appropriately selected from among, for example, a semiconductor laser, a light-emitting diode, a solid-state laser, and a gas laser. The light source 16 generates a light beam which has a specific wavelength falling within a range of 600 to 1,000 nm and which has the power spectrum of the secondary modulated signal shown in FIG. 3 (hereinafter the light beam may be referred to as a "modulated light beam").

In this first embodiment, as described above, each light emission section 1 is formed of six light generation units 10. In this case, the light sources 16 of the light generation units 10 generate modulated light beams having wavelengths of, for example, 695, 730, 780, 805, 830, and 950 nm.

The modulated light beams emitted from the light emission sections 1 are directed toward the interior of a living organism via a light mixer 17 (for example, an optical fiber). Notably, the light mixer 17 may be omitted. In such a case, the modulated light beams from the light emission sections 1 are supplied directly to the interior of a living organism.

Figure 4:
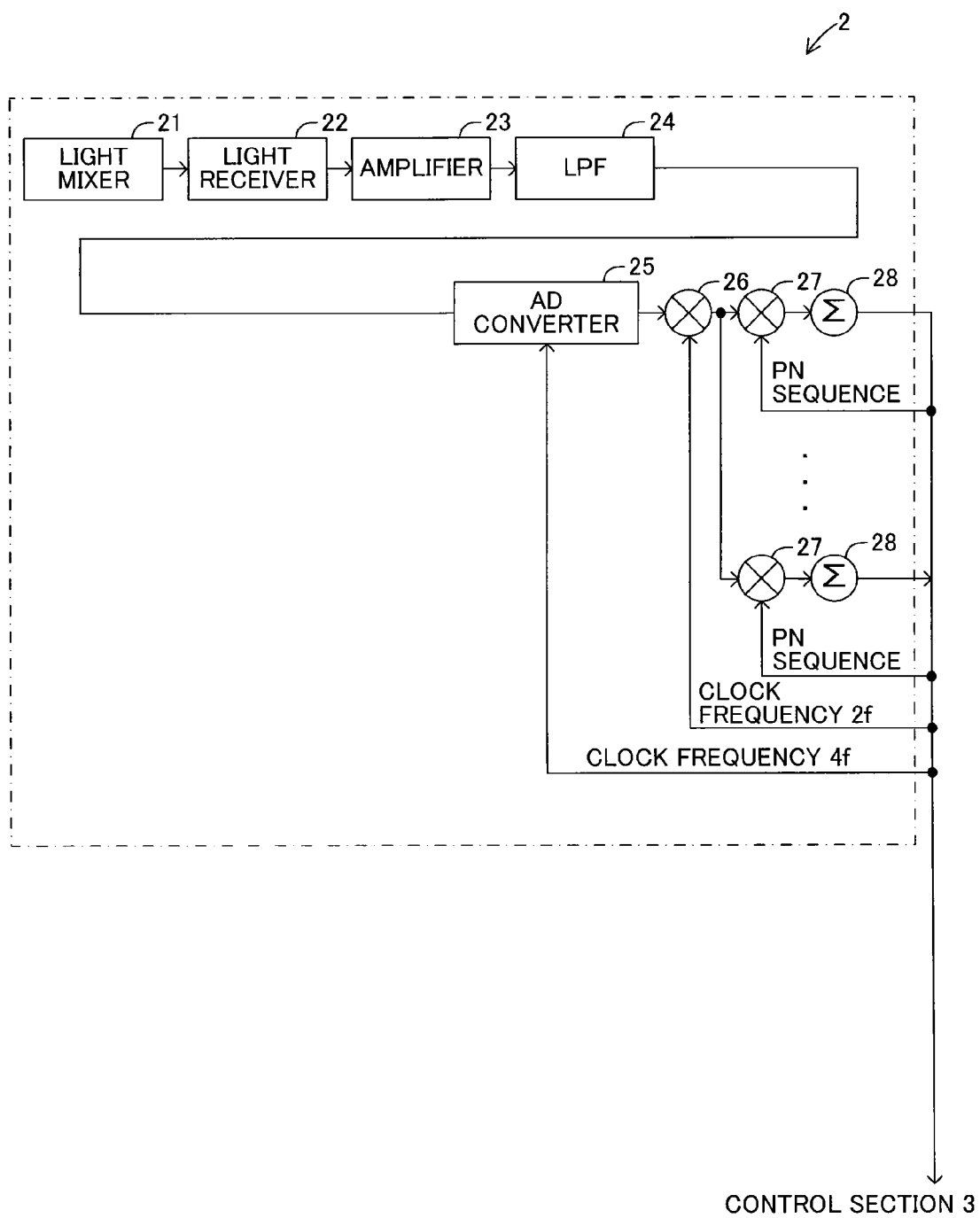
FIG. 4 is a block diagram schematically showing the configuration of a light detection section of FIG. 1.

As shown in FIG. 4, each light detection section 2 detects modulated light beams having propagated through the living organism while being reflected, and outputs biological information signals representing biological information carried by the detected modulated light beam. For such detecting operation, the light detection section 2 includes a light receiver 22, which receives, via a light mixer 21 (for example, an optical fiber), the modulated light beam having propagated through the living organism and having come out of the living organism. Notably, the light mixer 21 may be omitted. In such a case, the light receiver 22 directly receives the modulated light beam having propagated through the living organism and having come out of the living organism.

The light receiver 22 includes, for example, a photodiode or a photo multiplier as a main component, and its effective detection band width is set to 2f. The light receiver 22 outputs to an amplifier 23 electrical detection signals corresponding to the received modulated light beams in a time series fashion.

The amplifier 23 amplifiers each electrical detection signal (analog signal) output from the light receiver 22. As described above, the modulated light beams emitted from each of the light sources 16 of the light emission sections 1 are emitted on the basis of the corresponding secondary modulated signal. Therefore, the modulated light beam received by the light receiver 22 also has a power spectrum as shown in FIG. 3. That is, since the modulated light beam received by the light receiver 22 also has a power spectrum such that the DC component and the signal components of frequencies near DC are very small, the amplifier 23 amplifies the detection signal after removing from the received electrical detection signal the DC component and signal components of frequencies near DC.

Figure 5:
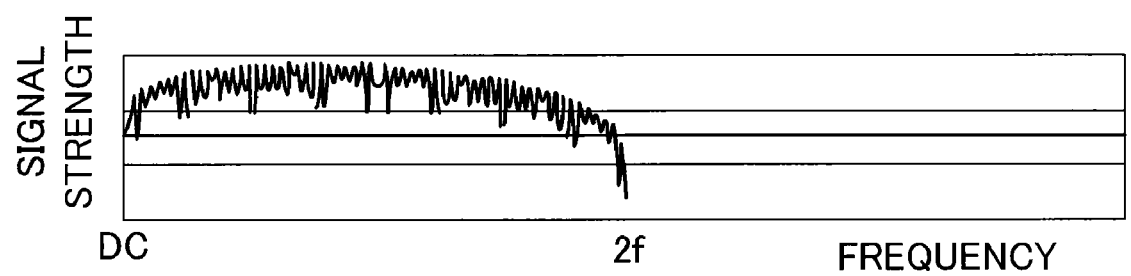
FIG. 5 is a graph showing the power spectrum of an electrical detection signal having passed through an LPF of FIG. 4.

The detection signal amplified by the amplifier 23 is output to a low-pass filter (LPF) 24. The cutoff frequency of the LPF 24 is set to 2f. Thus, the LPF 24 removes (cuts) signal components whose frequencies are higher than 2f from the detection signal received from the amplifier 23, and outputs a resultant electrical detection signal to an AD converter 25. FIG. 5 shows the power spectrum of the electrical detection signal having passed through the LPF 24. Notably, since the power spectrum of each of the modulated light beams emitted from the light emission sections 1 is such that the signal strength becomes very small near the frequency 2f as shown in FIG. 3, no problem arises even when the cutoff frequency of the LPF 24 is not precisely adjusted to 2f.

The AD converter 25 converts to a digital signal the electrical detection signal (analog signal) having passed through the LPF 24. Specifically, the AD converter 25 receives the clock signal of frequency 4f supplied from the clock generator 31 of the control section 3 and properly delayed by the delay circuit 32, and converts the electrical detection signal (analog signal) to a digital signal at a sampling frequency 4f. Since the AD converter 25 executes the digital conversion processing at the sampling frequency 4f, which is two times the effective detection band width 2f of the light receiver 22, the sampling theorem (also called Nyquist's theorem), which is generally known, stands.

According to the sampling theorem, in order to accurately reproduce a target signal, the signal must be sampled by use of a sampling frequency at least two times the frequency of the target signal. The "target signal" in the sampling theorem is the "electrical detection signal (analog signal)" corresponding to a modulated light beam having propagated through the living organism and received by the light receiver 22, and the "frequency of the target signal" in the sampling theorem is 2f, corresponding to the effective detection band width of the light receiver 22. Therefore, by means of setting the sampling frequency to 4f, the sampling theorem stands in the digital conversion processing performed by the AD converter 25. In other words, information (that is, the analog detection signal) carried by a modulated light beam corresponding to the effective detection band width of the light receiver 22 is accurately converted to a digital signal without causing dropping of the information or the like.

Upon completion of the conversion of the electrical detection signal (analog signal) to a digital signal at the sampling frequency 4f, the AD converter 25 outputs the digital signal to a first multiplier 26. The first multiplier 26 receives the digital signal, and receives the clock signal of frequency 2f supplied from the clock generator 31 and delayed by the delay circuit 32 of the control section 3. The first multiplier 26 demodulates the digital signal by use of the clock signal of frequency 2f received from the clock generator 31. In the following description, the signal demodulated by the first multiplier 26 will be referred to as the "primary demodulated signal." After completion of the demodulation of the digital signal, the first multiplier 26 outputs the primary demodulated signal to second multipliers 27.

Each of the second multipliers 27 computes the product of the primary demodulated signal received from the first multiplier 26 and the PN sequence supplied from the corresponding spread code sequence generator 11 of the light emission sections 1 and delayed by the delay circuit 32 of the control section 3. Since the second multiplier 27 obtains the PN sequence, the second multiplier 27 can demodulate, through spectrum despreading, the primary demodulated signal corresponding to the modulated light beam from a specific light emission section 1 of the plurality of light emission sections 1. The second multiplier 27 then outputs to a corresponding accumulator 28 the electrical detection signal demodulated through the spectrum despreading; i.e., a secondary demodulated signal.

The accumulator 28 accumulates the secondary demodulated signal over one or more periods of the PN sequence generated by the corresponding spread code sequence generator 11 of the light emission sections 1. Subsequently, the accumulator 28 outputs, to the control section 3, a biological information signal corresponding to a modulated light beam which has been emitted from the specific light emission section 1 and attenuated in the living organism; i.e., a modulated light beam containing biological information. As shown in FIG. 4, the second multipliers 27 and the accumulators 28 are provided such that their numbers are equal to the number of specific waveforms emitted from the light emission section 1 (in the present embodiment, six second multipliers 27 and six accumulators 28 are provided for each light emission section 1; in the case where light beams can be received from a plurality of light emission sections 1, the numbers of the second multipliers 27 and the accumulators 28 are equal to the number obtained by multiplying 6 by the number of the light emission sections 1). Thus, biological information signals corresponding to modulated light beams having propagated through the living organism can be obtained simultaneously.

Figure 6:
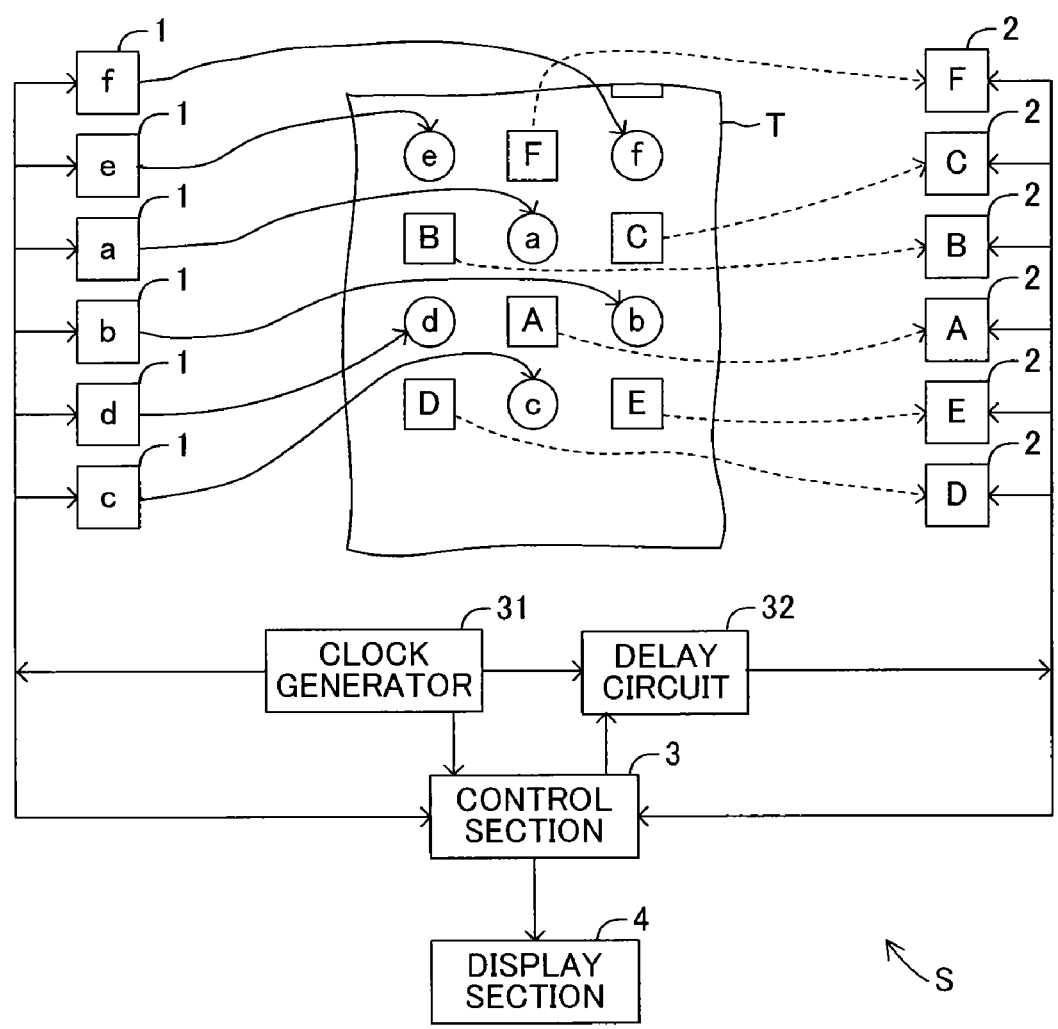
FIG. 6 shows a part of the arrangement of incident points and light-receiving points in the case where the biological information measuring apparatus of FIG. 1 is applied to measurement of blood oxygen level in the brain.

The biological information measuring apparatus S, which has the above-described configuration, will now be described by taking, as an example, the case where the blood oxygen level in the brain (i.e., biological information) is measured through operational control of the control section 3. When the blood oxygen level in the brain is measured, as shown in FIG. 6, modulated light beams emitted from the light emission sections 1 are supplied to circular points a to f (hereinafter may be referred to as "incident points a to f") on the surface of a head T. The light detection sections 2 detect the modulated light beams (hereinafter may be referred to as "reflected light beams") which have propagated through the head T and have reached square points A to F (hereinafter may be referred to as "light-receiving points A to F"). The incident points a to f and the light-receiving points A to F are arranged in the form of a matrix. In the following description of operation, the light emission sections 1 which emit modulated light beams to the incident points a to f will be respectively called "light emission sections a to f," and the light detection sections 2 which detect reflected light beams which have reached the light-receiving points A to F will be respectively called "light detection sections A to F."

FIG. 6 shows only a part of the biological information measuring apparatus S. Therefore, the number of the incident points and the light-receiving points (i.e., the number of channels) is not limited to the number shown in FIG. 6, and the blood oxygen level in the brain can be measured by use of a greater number of incident points and light-receiving points which are arranged in the form of a matrix. The arrangement of the channels is not limited to the matrix arrangement, and the channels may be arranged in a staggered pattern, or in an annular pattern such that a plurality of light detection sections 2 are disposed around a light emission section 1.

Emission of light beams by the light emission sections a to f will now be described. An operator operates a non-illustrated input apparatus, and gives an instruction to the control section 3 for designating a specific wavelength of modulated light beams to be injected into the head T. In this case, the operator can give an instruction to the control section 3 for specifying a plurality of specific wavelengths of modulated light beams to be emitted. According to this instruction, the control section 3 operates the base band output units 13 of the light emission sections a to f for generating modulated light beams having the above-designated specific wavelengths. As a result, the light generation units 10 initiate their operations for generating modulated light beams having the above-designated specific wavelengths.

Specifically, in each of the light generation units 10 of the light emission sections a to f, the spread code sequence generator 11 generates, for example, a Gold code sequence as a PN sequence. Subsequently, the spread code sequence generator 11 outputs the thus-generated PN sequence to the control section 3, as well as to the first multiplier 12. The first multiplier 12 calculates the product of the PN sequence and the DC signal (base band signal) supplied from the corresponding base band output unit 13, to thereby spread-spectrum modulate the DC signal.

Subsequently, the primary modulated signal produced through the spread spectrum modulation is supplied to the second multiplier 14. The second multiplier 14 modulates the primary modulated signal by use of the clock signal of frequency 2f supplied from the clock generator 31 to thereby produce a secondary modulated signal, and supplies the secondary modulated signal to the corresponding light source driver 15. Thus, the light sources 16 (e.g., semiconductor lasers) of the light emission sections a to f emit modulated light beams having the specific wavelengths to the incident points a to f. The modulated light beams injected through the incident points a to f pass through the skull of the head T, enter the cerebral cortical layer, and propagate through the cerebral cortical layer while being diffusely reflected (i.e., being attenuated). Subsequently, the modulated light beams again pass through the skull of the head T, and reach the surface of the head T.

Detection of reflected light beams by the light detection sections A to F will next be described. The modulated light beams which have reached the surface of the head T are detected as reflected light beams by the light detection sections A to F via the light-receiving points A to F. In the light detection sections A to F, the respective light receivers 22 receive all the reflected light beams having reached the light-receiving points A to F, and outputs an electrical detection signal corresponding to each of the received reflected light beams to the amplifier 23 in a time series manner. After removing the DC signal component and signal components of frequencies near DC from the received electrical detection signal, the amplifier 23 amplifies the electrical detection signal. The amplified detection signal is passed through the LPF 24, whereby signal components whose frequencies are higher than 2f are removed.

Subsequently, the AD converter 25 converts the electrical detection signal (analog signal) having passed through the LPF 24 to a digital signal at the sampling frequency 4f. The electrical detection signal having undergone the digital conversion processing is supplied to the first multiplier 26. The first multiplier 26 demodulates the received electrical detection signal (digital signal) by use of the clock signal of frequency 2f, and outputs the demodulated detection signal; i.e., the first demodulated signal, to the second multipliers 27. When the demodulation processing is performed in this manner, the demodulated signal becomes a signal which uses the entirety of the effective detection band width 2f of the light receiver 22. In other words, it is possible to output to the second multipliers 27 the primary demodulated signal, which is a digital signal which accurately represents information carried by the modulated light beams which can be received by the light receiver 22; i.e., the state of attenuation of modulated light beams having propagated through the cerebral cortical layer, without causing dropping of the information.

Incidentally, the modulated light beams injected through the incident points a to f reach the light-receiving points A to F as reflected light beams. For example, light beams which reach the light-receiving point A, as reflected light beams, include not only the modulated light beams injected through the incident points a, b, c, and d, which are located around the light-receiving point A, but also the modulated light beams injected through the incident points e and f. Under this circumstance, the control section 3 controls the light detection section A such that the section A obtains pieces of biological information corresponding to, for example, reflected light beams corresponding to the modulated light beams injected through the incident points a, b, c, and d, among all the reflected light beams that have reached the light-receiving point A. Operation of the control section 3 for the above control will next be described specifically.

As described above, the control section 3 obtains PN sequences from the spread code sequence generators 11 of each light generation unit 10. Meanwhile, the second multipliers 27 of the light detection section 2 obtain, via the control section 3, the PN sequences generated by the spread code sequence generators 11 of the light emission sections a to f. At that time, the control section 3 supplies different PN sequences, generated by the spread code sequence generators 11 of the light emission sections a, b, c, and d, to the corresponding second multipliers 27 of the light-receiving point A.

Each second multiplier 27 computes the product of the primary demodulated signal output from the first multiplier 26 and the corresponding PN sequence supplied from the control section 3; that is, subjects the primary demodulated signal to spectrum despreading, to thereby obtain the secondary demodulated signal, and outputs the secondary demodulated signal to the corresponding accumulator 28. The accumulator 28 accumulates the secondary demodulated signal over one or more periods of the PN sequence. As described above, through the sum-of-product processing performed for the emitted modulated light beams by the second multiplier 27 and the accumulator 28, the correlation between the secondary demodulated signal and the supplied PN sequence can be obtained, whereby a plurality of pieces of biological information corresponding to the plurality of modulated light beams emitted from the light emission sections a, b, c, and d, respectively, can be output simultaneously.

As described above, two different PN sequences are orthogonal with each other; i.e., the product of the different PN sequences becomes "0." Therefore, when the control section 3 supplies to a certain second multiplier 27 the PN sequence generated by the corresponding spread code sequence generator 11 of, for example, the light emission section a, the product of the PN sequence of the light emission section a and the primary demodulated signals output from the first multiplier 26, other than the primary demodulated signal corresponding to the specific modulated light beam emitted from the light emission section a, becomes "0." Therefore, the secondary demodulated signal obtained through accumulation by the corresponding accumulator 28 over at least one period of the PN sequence becomes "0," and the correlation becomes "0."

Thus, primary modulated signals and secondary demodulated signals (that is, biological information signals) which do not have (or do not coincide with) the PN sequence supplied from the control section 3 are selectively eliminated, and only the biological information corresponding to the reflected light beam of the specific modulated light beam emitted from the light emission section a is output from the specific second multiplier 27 and accumulator 28. Similarly, the control section 3 supplies to the remaining second multipliers 27 the PN sequences generated by other corresponding spread code sequence generators 11 of the light emission section a, whereby these second multipliers 27 and accumulators 28 simultaneously output to the control section 3 pieces of biological information corresponding to the reflected light beams of other specific modulated light beams emitted from the light emission section a. Further, when PN sequences of the remaining light emission sections b, c, and d are supplied from the control section 3 to the second multipliers 27, pieces of biological information corresponding to the reflected light beams of the plurality of modulated light beams emitted from the light emission sections b, c, and d are simultaneously output to the control section 3.

Thus, the light detection section A outputs to the control section 3 pieces of biological information corresponding to the reflected light beams of the modulated light beams emitted from the light emission sections a to d, among the modulated light beams emitted from the light emission sections a to f and having the specific wavelengths. Similar to the case of the light detection section A, the light detection sections B to F are controlled by the control section 3. Therefore, pieces of biological information corresponding the reflected light beams of the modulated light beams emitted from specific light emission sections of the light emission sections a to f can be simultaneously output.

When other specific wavelengths (total six specific wavelengths in the present embodiment) of modulated light beams to be injected into the head T are designated by the operator, the control section 3 repeatedly performs operational control in a manner similar to the aforementioned operational control, for modulated light beams having the thus-designated specific wavelengths, respectively. Thus, each of the light detection sections A to F can simultaneously output, to the control section 3, pieces of biological information corresponding to the reflected light beams emitted from the plurality of specific light emission sections among the reflected light beams of the modulated light beams emitted from the light emission sections a to f and having other specific wavelengths.

When the biological information signals are output from the light detection sections A to F, the control section 3 calculates the blood oxygen level in the brain (i.e., subject) on the basis of the thus-output biological information signals, and outputs the thus-calculated blood oxygen level to the display section 4. The display section 4 displays the blood oxygen level in the brain in a predetermined mode. Detailed description of the method for calculating the blood oxygen level is omitted, since the calculation method is not related directly to the present invention. However, the blood oxygen level calculation method will next be described briefly.

In the present embodiment, according to the Lambert-Beer law representing the relation between concentration and light attenuation, the blood oxygen level is calculated on the basis of the attenuation of modulated light beams caused by the difference in blood hemoglobin levels; i.e., the degree of absorption of the modulated light beams by hemoglobin. Hemoglobin in blood, which binds to oxygen and flows through blood vessels, plays a role in supplying oxygen to cells. Therefore, in blood flowing through arteries, the level of hemoglobin bound to oxygen (hereinafter may be referred to as "oxidized hemoglobin") is high, whereas in blood flowing veins, the level of hemoglobin not bound to oxygen (hereinafter may be referred to as "reduced hemoglobin") is high.

Figure 7:
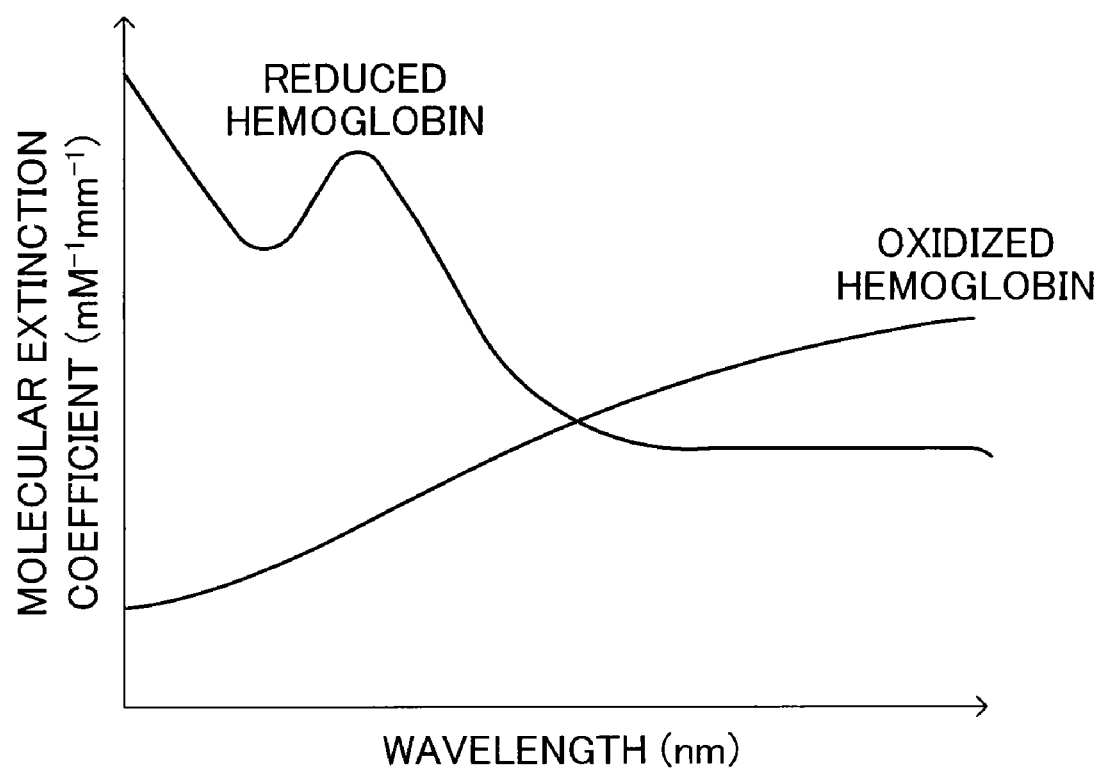
FIG. 7 is a graph schematically showing change in the molecular extinction coefficient of oxidized hemoglobin or reduced hemoglobin with respect to wavelength.

As schematically shown in FIG. 7, each of oxidized hemoglobin and reduced hemoglobin which are present in blood exhibits an optical absorption spectrum in which the molecular extinction coefficient nonlinearly varies with respect to the wavelengths of emitted light beams (modulated light beams). The blood oxygen level in arteries, capillaries, or veins can be calculated according to the optical absorption spectra of oxidized hemoglobin and reduced hemoglobin; i.e., the Lambert-Beer law employing the molecular extinction coefficient, the intensities of emitted light beams (modulated light beams), and the intensities of light beams reflected by oxidized hemoglobin or reduced hemoglobin.

According to the Lambert-Beer law, the control section 3 can calculate the blood oxygen level in arteries or veins (particularly in capillary vessels) more accurately and in more detail by use of the molecular extinction coefficients corresponding to the six specific wavelengths, the emission intensities of the modulated light beams having the six specific wavelengths, and the intensities of the reflected light beams having the six specific wavelengths represented by the biological information signals output from the light detection sections A to F.

The control section 3 supplies the calculated blood oxygen level in arteries, capillaries, or veins to the display section 4, and instructs the display section 4 to display the blood oxygen level in a predetermined display mode. In accordance with this instruction, the display section 4 displays the blood oxygen level on the display in the predetermined display mode. The display section 4 displays the blood oxygen level in display modes which will be described below.

For example, as described above, a certain light detection section 2 (e.g., the light detection section A) can identify specific light emission sections 1 (e.g., the light emission sections a to d) of the plurality of light emission sections 1, and selectively detect reflected light beams of modulated light beams emitted from the thus-identified light emission sections 1. Therefore, measurement points can be densely arranged; i.e., the resolution of the measurement points can be improved considerably. Therefore, the control section 3 can calculate the blood oxygen levels at the measurement points distributed along a plane. Therefore, in this case, the display section 4 displays the blood oxygen levels supplied from the control section 3 in a two-dimensional display mode, whereby change in blood flow associated with cerebral activity can be observed in detail.

Notably, when a specific wavelength (e.g., 830 nm or 780 nm) falling within a range in which the molecular extinction coefficient significantly varies in a nonlinear manner (see FIG. 7) is designated by the operator, the light emission sections a to f emit a modulated light beam having the thus-designated specific wavelength. Therefore, even in the case where modulated light beams have wavelengths falling within a range in which the molecular extinction coefficient varies in a nonlinear manner, when the detection signals output from the light detection sections A to F are employed, change in the blood oxygen level in arteries, capillaries, or veins can be accurately detected.

Further, as described above, when the control section 3 changes PN sequences output to the second multipliers 27 of the light detection sections 2, the light detection sections 2 can selectively switch the light emission sections 1 to be identified. Thus, the blood oxygen level in the brain can be measured in a three-dimensional manner. In general, when a light beam is emitted from an emission point at a predetermined angle to a reflection object, the point which the reflected light beam reaches varies depending on the distance between the emission point and the reflection object. Specifically, in the case where a light beam is emitted from an emission point to a reflection object, when the distance between the emission point and the reflection object is small, the point which the reflected light beam reaches is close to the emission point; i.e., is located at a shallow position in the cerebral cortical layer. Meanwhile, when the distance between the emission point and the reflection object is large, the point which the reflected light beam reaches is away from the emission point; i.e., is located at a deep position in the cerebral cortical layer. Even when modulated light beams are injected into the head T as described above, the above-described tendency generally occurs, although the paths of the reflected light beams cannot be strictly specified due to diffuse reflection of the modulated light beams in the head T.

Therefore, in the biological information measuring apparatus S according to the present embodiment, when the control section 3 causes the light detection section 2 to identify the light emission sections 1 such that the light detection section 2 and the light emission sections 1 have different distances therebetween, the blood oxygen level can be measured in a depth direction. Accordingly, in this case, the display section 4 displays the blood oxygen levels supplied from the control section 3 in a three-dimensional display mode. Since the blood oxygen level in arteries, capillaries, or veins within the brain is displayed three-dimensionally, change in blood flow associated with cerebral activity can be observed three-dimensionally.

As can be understood from the above description, according to the first embodiment, the second multiplier 14, which serves as the second modulation means, generates the secondary modulated signal at the frequency 2f (second frequency) two times the frequency f (first frequency) (i.e., the chip rate f). Therefore, the secondary modulated signal can have a power spectrum such that the center of its main lobe is located at the frequency f, and the main lobe extends from the frequencies at DC and near DC to the frequency 2f. As a result, the output (intensity) of a near-infrared light beam emitted from each light generation unit 10 becomes very small at DC, frequencies near DC, and the frequency 2f. Accordingly, through use of the near-infrared light beam emitted from the light emission sections 1, the DC problems associated with spectrum spreading can be avoided efficiently.

The signal bandwidth of the electrical detection signal (analog signal), from which the DC component and signal components of frequencies near DC and frequencies higher than the frequency 2f have been removed by the amplifier 23 and the LPF 24, which serve as the signal component removal means, coincides with the effective detection band width 2f of the light receiver 22. As a result, the effective detection band width 2f of the light receiver 22 can be utilized very efficiently.

The AD converter 25, which serves as the signal conversion means, converts the electrical detection signal (analog signal) output from the LPF 24 to a digital signal by using a clock signal whose frequency (sampling frequency; third frequency) 4f is two times the frequency 2f and which is delayed by the delay circuit 32. In other words, the AD converter 25 converts the analog signal to a digital signal at the sampling frequency 4f two times the effective detection band width 2f of the light receiver 22. As described above, since the analog signal is converted to a digital signal at the sampling frequency 4f two times the effective detection band width 2f of the light receiver 22; i.e., two times the signal band of the analog signal, biological information carried by the analog signal corresponding to the entirety of the effective detection band width of the light receiver 22 can be reproduced well as a digital signal. Thus, the efficiency of use of frequencies in spectrum spreading can be greatly improved.

As described above, when biological information is measured by use of the biological information measuring apparatus S, the influence of the DC problems associated with spectrum spreading can be eliminated, and the efficiency of use of frequencies required for emission and detection of near-infrared light and conversion of the detected near-infra- b. Second Embodiment

In the above-described first embodiment, each base band output unit 13 of each light emission section 1 outputs a DC signal, and the corresponding first multiplier 12 multiplies the DC signal by a PN sequence supplied from the corresponding spread code sequence generator 11. Thus, the DC signal is spread-spectrum modulated, whereby the primary modulated signal is generated. However, the present invention can be practiced in such a manner that, instead of modulating a DC signal through spread spectrum modulation, a signal including rectangular pulses generated at an arbitrary clock frequency is modulated thought spread spectrum modulation. This second embodiment will now be described in detail. Portions identical with those of the first embodiment are denoted by the same reference numerals, and their descriptions will be omitted.

Figure 8:
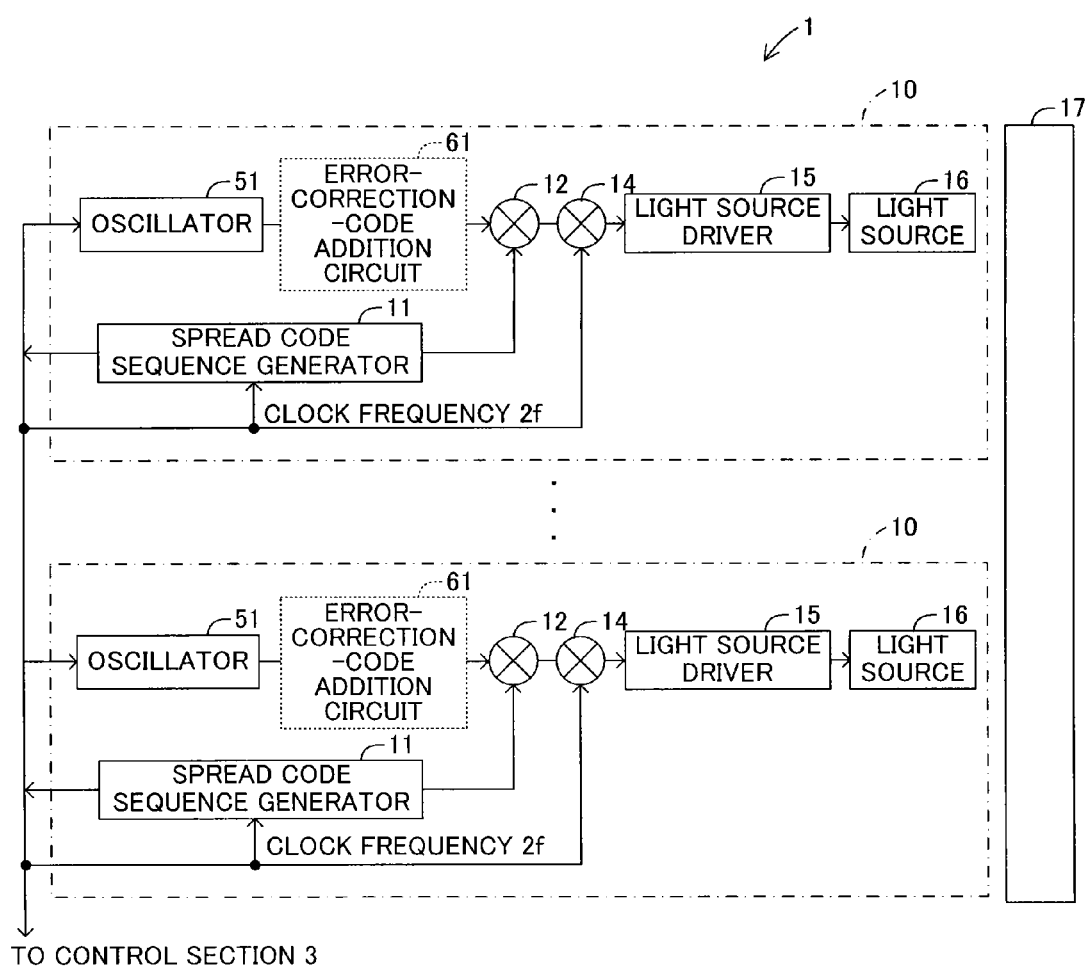
FIG. 8 is a block diagram schematically showing the configuration of a light emission section according to a second embodiment of the present invention.

As shown in FIG. 8, a biological information measuring apparatus S according to the second embodiment includes oscillators 51 in place of the base band output units 13 of the light emission sections 1, used in the first embodiment shown in FIG. 1. Each of the oscillators 51 operates at a previously set arbitrary frequency equal to or less than half the frequency of clocks generated by the clock generator 31 (more specifically, frequency equal to or less than half the frequency f, which is the first frequency), and outputs a rectangular signal which has a predetermined amplitude and serves as the base band signal. The oscillator 51 outputs the generated rectangular signal to the corresponding first multiplier 12. As a result, as in the above-described first embodiment, the first multiplier 12 modulates the rectangular signal through spread spectrum modulation by calculating the product of the rectangular signal output from the oscillator 51 and the PN sequence supplied by the corresponding spread code sequence generator 11, and outputs the modulated rectangular signal to the second multiplier 14 as the primary modulated signal.

Figure 9:
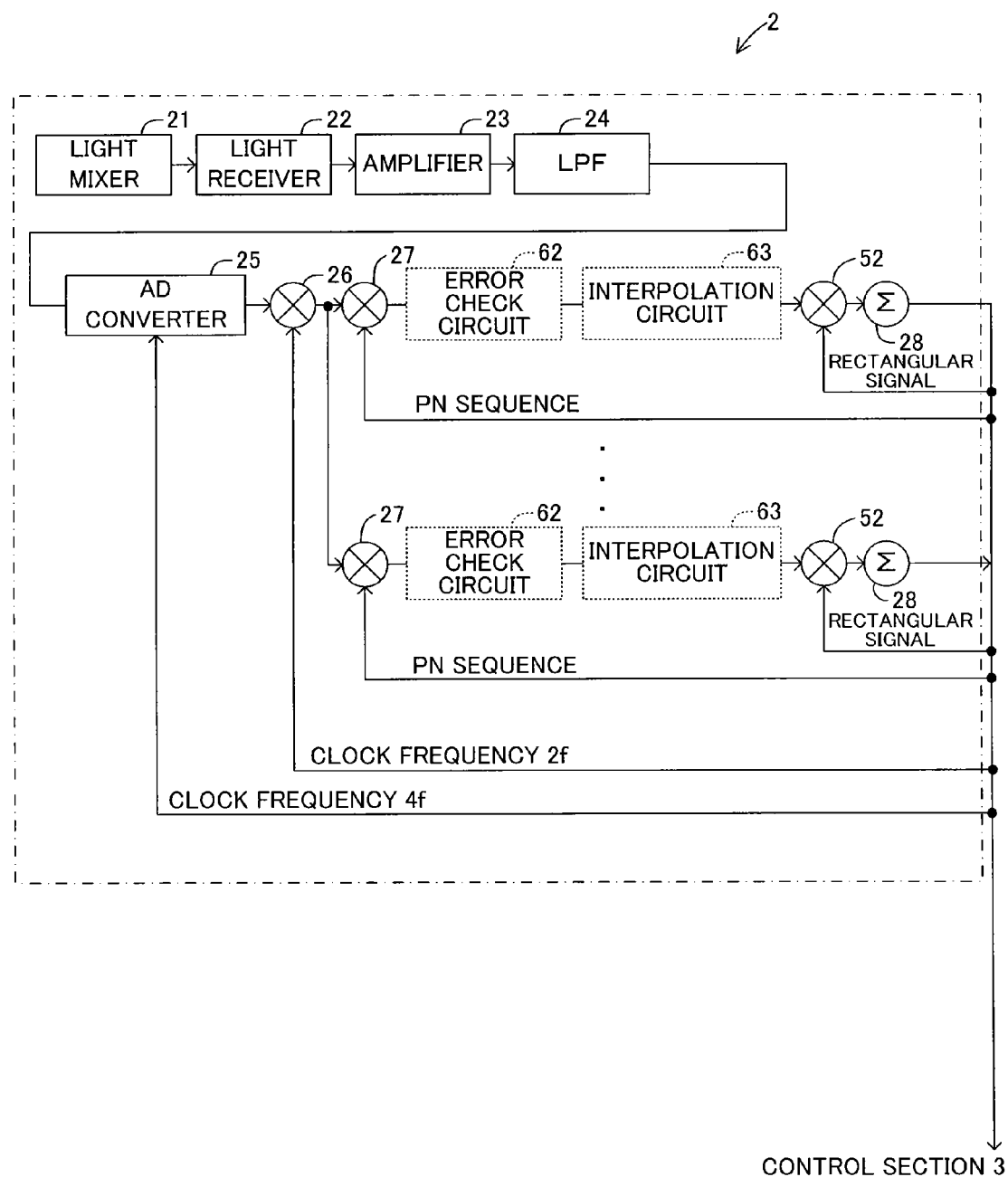
FIG. 9 is a block diagram schematically showing the configuration of a light detection section according to the second embodiment of the present invention.
Figure 11:
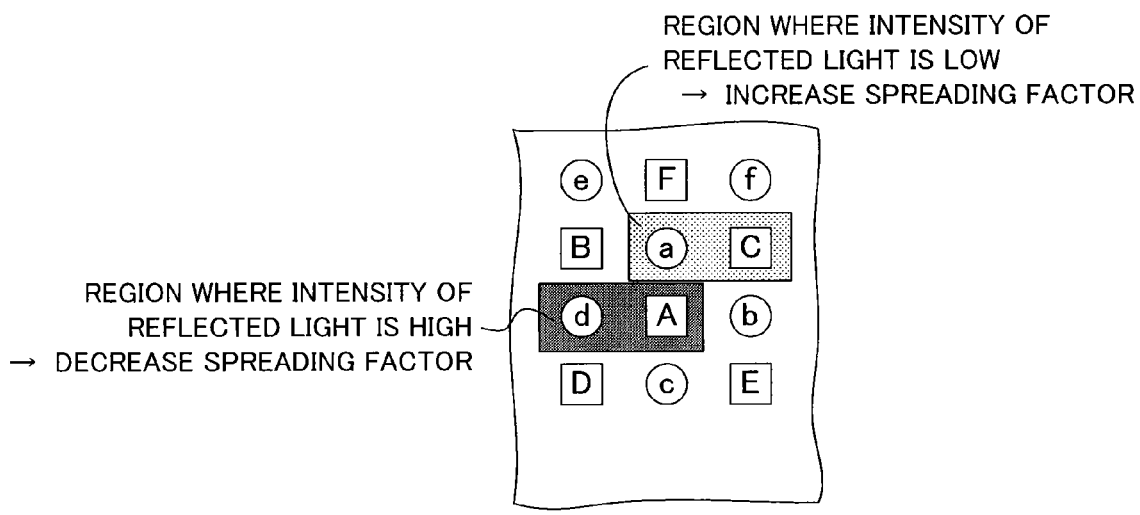
FIG. 11 relates to the third embodiment of the present invention and is used for describing a situation where the spreading factor is changed.

Further, as shown in FIG. 9, the light detection section 2 of the biological information measuring apparatus S according to the second embodiment differs from that of the first embodiment shown in FIG. 4 in that third multipliers 52 are added. Each of the third multipliers 52 effects demodulation through calculation of the product of the secondary demodulated signal received from the corresponding second multiplier 27 and including the base band signal (the rectangular signal generated by the corresponding oscillator 51) and the rectangular signal supplied from the corresponding oscillator 51 of the light emission sections 1 via the delay circuit 32 of the control section 3, while being delayed by the delay circuit 32, to thereby calculate a value of an amplitude component resenting the influence which the corresponding modulated light beam receives from the biological organism when it propagates therethrough; i.e., the degree of attenuation of the modulated light beam. The third multiplier 52 outputs the value of the amplitude component to the corresponding accumulator 28.

In the second embodiment having the above-described configuration, the control section 3 controls its operation in the same manner as the first embodiment, whereby the second embodiment is expected to achieve the same effects as the first embodiment.

c. Modification of Second Embodiment

In the above-described second embodiment, the rectangular signal output from each oscillator 51 of the light emission sections 1 is directly modulated by the corresponding first multiplier 12 through spread spectrum modulation. However, the second embodiment may be practiced such that error correction is executed between transmitted signals and received signals so as to obtain a more accurate biological information signal.

As shown by broken lines in FIG. 8, in this modification of the second embodiment, error-correction-code addition circuits 61 are added, which add error correction codes to the rectangular signals output from the oscillators 51 of the second embodiment. Each of the error-correction-code addition circuits 61 adds, to the rectangular signal (i.e., bit string) output from the corresponding oscillator 51, an error correction code bit string for each string of a previously set arbitrary number of bits. Examples of the error correction code include known CRC (Cyclic Redundancy Check) code and parity code.

As shown by broken lines in FIG. 9, the light detection section 2 according the modification of the second embodiment includes an error check circuit 62 and an interpolation circuit 63. The error check circuit 62 checks the consistency of the secondary demodulated circuit (data sequence) to which an error correction code was added by the corresponding error-correction-code addition circuit 61, and corrects the error. When the error check circuit 62 fails to correct the error, the interpolation circuit 63 replaces the data sequence with a correct data sequence.

Specifically, the error check circuit 62 checks the consistency of the secondary demodulated signal on the basis of the secondary demodulated signal output from the corresponding second multiplier 27 and containing the base band signal (i.e., the rectangular signal which was generated by the corresponding oscillator 51 and to which an error correction code was added by the corresponding error-correction-code addition circuit 61), and the rectangular signal supplied from the corresponding oscillator 51 of the light emission sections 1 via the delay circuit 32 of the control section 3, while being delayed by the delay circuit 32. When the data sequence in the secondary demodulated signal is correct, the error check circuit 62 outputs the secondary demodulated signal to the interpolation circuit 63 without restoring it. When the data sequence in the secondary demodulated signal contains an error but it can be restored, the error check circuit 62 restores the relevant bit of the data sequence containing the error, and then outputs the secondary demodulated signal to the interpolation circuit 63. When the data sequence in the secondary demodulated signal contains an error and it cannot be restored, the error check circuit 62 outputs the secondary demodulated signal to the interpolation circuit 63 as it is.

The interpolation circuit 63 performs interpolation processing for the secondary demodulated signal which cannot be restored by the error check circuit 62, on the basis of the secondary demodulated signal supplied from the error check circuit 62 and having undergone the consistency checking, and the rectangular signal supplied from the corresponding oscillator 51 of the light emission sections 1 via the delay circuit 32 of the control section 3, while being delayed by the delay circuit 32. For the secondary demodulated signal determined by the error check circuit 62 that it includes a correct data sequence; i.e., it is not required to be restored and the secondary demodulated signal having undergone the bit restoration by the error check circuit 62, the interpolation circuit 63 outputs the secondary demodulated signal to the third multiplier 52. Further, for the secondary demodulated signal including an incorrect data sequence, which cannot be restored by the error check circuit 62, the interpolation circuit 63 outputs the secondary demodulated signal to the third multiplier 52 after replacing the erroneous data sequence with a correct data sequence. Specifically, the interpolation circuit 63 restores the incorrect data sequence by, for example, replacing the data sequence including incorrect data with a correct data sequence which has arrived last among data sequences containing error data, or a correct data sequence before or after the incorrect data sequence, which is the unit of data sequence to which an error correction code is added by the error-correction-code addition circuit 61.

The third multiplier 52 receives the secondary demodulated signal containing a correct data sequence from the interpolation circuit 63. Subsequently, in the same manner as in the second embodiment, the third multiplier 52 demodulates the secondary demodulated signal by calculating the product of the received secondary demodulated signal and the rectangular signal supplied from the corresponding oscillator 51 of the light emission sections 1 via the delay circuit 32 of the control section 3, while being delayed by the delay circuit 32, to thereby calculate the value of an amplitude component resenting the influence which the corresponding modulated light beam receives from the biological organism when it propagates therethrough; i.e., the degree of attenuation of the modulated light beam. The third multiplier 52 outputs the value of the amplitude component to the corresponding accumulator 28.

In the modification of the second embodiment having the above-described configuration, the control section 3 controls its operation in the same manner as the first embodiment, whereby the second embodiment is expected to achieve the same effects as the first embodiment. Further, in the modification of the second embodiment, since the consistency between the modulated light beams emitted from the light emission sections 1 and the modulated light beams detected by the light detection section 2 and including biological information signals can be checked, the biological information signals can be obtained more accurately.

c. Third Embodiment

In the above-described first and second embodiments, each of the spread code sequence generators 11 always generates the PN sequence at a constant spreading factor. Here, the term "spreading factor" refers to a value obtained by dividing the time of one period of the generated PN sequence by the reciprocal of a chip rate.

Incidentally, the spread spectrum modulation has characteristics as follows. When the spreading factor is increased, the SN ratio of a signal obtained through spectrum dispreading; i.e., demodulation, increases, although the signal bandwidth becomes narrower. In contrast, when the spreading factor is decreased, the signal bandwidth of a signal obtained through spectrum dispreading becomes wider, although the SN ratio of the signal decreases. By making use of such characteristics of the spread spectrum modulation, the light detection section 2 can detect modulated light beams well. This third embodiment will now be described in detail. Portions identical with those of the first and second embodiments are denoted by the same reference numerals, and their descriptions will be omitted. Notably, since this third embodiment can be applied to the first and second embodiments, the case where the third embodiment is applied to the first embodiment will be described as an example.

As described above, when a modulated light beam having a specific wavelength is emitted from the light emission section 1 into a living organism, the strength of the modulated light beam (i.e., a detection signal) detected by the light detection section 2 changes depending on the incident position of the light beam, because the manner of absorption and scattering of the modulated light beam during propagation through the living organism. That is, when a modulated light beam having entered the living organism from a certain position is absorbed and scattered to a small degree during the propagation, the strength of the detection signal detected by the light detection section 2 may be large. In contrast, when a modulated light beam having entered the living organism from a different position is absorbed and scattered to a large degree during the propagation, the strength of the detection signal detected by the light detection section 2 may be small.

When a difference arises between the strengths of two detection signals as described above, an operator instructs the control section 3 to change the spreading factor employed by a spread code sequence generator 11 of the light emission sections 1 which corresponds to the detection signal detected by the light receiver 22 of the light detection section 2 and having a low strength; i.e., SN ratio, to a CRI larger than a standard value CRc. Meanwhile, the operator instructs the control section 3 to change the spreading factor employed by a spread code sequence generator 11 of the light emission sections 1 which corresponds to the detection signal detected by the light receiver 22 of the light detection section 2 and having a high strength; i.e., SN ratio, to a CRs smaller than the standard value CRc. The standard value CRc represents a spreading factor which serves as a reference, and is typically set to $2^{16}$ (65536). CRI is set to about $2^{17}$ to $2^{32}$, and CRs is set to about $2^4$ to $2^{15}$. Notably, no limitation is imposed on the setting of the values of CRc, CRI, and CRs, and, needless to say, CRc, CRI, and CRs can be set to various values.

According to an instruction from the operator, the control section 3 changes the spreading factor to CRI or CRs, which is employed by each spread code sequence generator 11 to generate the PN sequence. By virtue of this operation, in the light emission section 1 corresponding to a detection signal whose SN ratio is determined to be low, the spreading factor CRc of the spread code sequence generator 11 is changed to CRI larger than CRc, whereby the SN ratio of a corresponding biological information signal is improved although the signal bandwidth of the biological information signal becomes narrower. Meanwhile, in the light emission section 1 corresponding to a detection signal whose SN ratio is determined to be high, the spreading factor CRc of the spread code sequence generator 11 is changed to CRs smaller than CRc, whereby the signal bandwidth of a corresponding biological information signal becomes wider, although the SN ratio of the signal slightly decreases. Therefore, biological information in a wide band can be obtained.

Incidentally, in general, the orthogonality in spread spectrum modulation which uses the above-described PN sequence (e.g., Hadamard sequence, M sequence, or Gold code sequence) is guaranteed when a fixed spreading factor is used. Therefore, in the case where modulated light beams which differ in spreading factor are emitted into a living organism, the orthogonality between these modulated light beams is possibly not guaranteed. Therefore, in this third embodiment, each spread code sequence generator 11 employs, as the PN sequence, an orthogonal variable spreading factor (OVSF) code which can guarantee the orthogonality between modulated light beams which differ in spreading factor.

This orthogonal variable spreading factor code is known to enable the spreading factor to be successively and regularly changed from 1 to $2^{(n+1)}$, as shown in FIG. 10. Further, it is well know that, through employment of the orthogonal variable spreading factor code, the orthogonality between modulated light beams is guaranteed not only when the modulated light beams have the same spreading factor but also when the modulated light beams have different spreading factors. Therefore, in the third embodiment, each spread code sequence generator 11 employs this orthogonal variable spreading factor code as the PN sequence, to thereby guarantee the orthogonality between modulated light beams, even when the modulated light beams are simultaneously emitted into a living organism while their spreading factors are made different from each other.

Thus, even in the case where the light emission sections 1 and the light detection sections 2 are arranged such that a region in which the strength of a detection signal is high is located adjacent to a region in which the strength of a detection signal is low, modulated light beams do not influence (interfere) each other. Accordingly, corresponding secondary demodulated signals can be obtained considerably satisfactorily, and accurate biological information signals can be obtained.

The present invention is not limited to the above-described first through third embodiments, and various modifications may be made without departing from the scope of the present invention.

For example, in the above-described embodiments, the biological information measuring apparatus S is applied to the case where the blood oxygen level is calculated as biological information by utilizing light absorbing characteristics of blood. However, needless to say, the measuring apparatus can measure other light absorbing characteristics, such as biological density, water content, blood glucose level, and lipid content, or light absorbing characteristics associated with changes, such as pulse, for example, oxygen saturation, by appropriately varying the specific wavelengths of light beams generated by a plurality of the light generation units 10 constituting the light emission sections 1. Thus, even when other light absorbing characteristics are utilized, biological information can be calculated more accurately through use of the biological information measuring apparatus S of the present invention.

What is claimed is:

1. A biological information measuring apparatus comprising a light emission section and a light detection section, wherein the light emission section includes:
base-band-signal output means for generating and outputting a predetermined base band signal;
spread-code-sequence generation means for generating a spread code sequence at a first frequency, the spread code sequence being used for modulating the base band signal through spread spectrum modulation;
first modulation means for spectrum-spreading the base band signal by using the spread code sequence generated by the spread-code-sequence generation means, to thereby output a primary modulated signal;
second modulation means for modulating the primary modulated signal output from the first modulation means by using a clock signal of a second frequency two times the first frequency, to thereby output a secondary modulated signal; and
light generation means having at least one light source and emitting an near-infrared light beam into a living organism, the near-infrared light beam being generated on the basis of the secondary modulated signal output from the second modulation means and having a specific wavelength, and the light detection section includes:
light receiving means for receiving the near-infrared light beam having been emitted from the light emission section and propagated through the living organism, converting the received near-infrared light beam to an electrical detection signal, and outputting the electrical detection signal;
signal component removal means for removing from the electrical detection signal a DC component, signal components of frequencies near DC, and signal components of frequencies equal to or higher than the second frequency, and outputting the electrical detection signal;
signal conversion means for converting the electrical detection signal output from the signal component removal means to a digital signal by using a clock signal of a third frequency two times the second frequency, the clock signal of the third frequency being supplied in consideration of a delay of the near-infrared light beam produced due to propagation of the near-infrared light beam through the living organism;
first demodulation means for demodulating the digital signal by using the clock signal of the second frequency, to thereby output a primary demodulated signal, the clock signal of the second frequency being supplied in consideration of the delay of the near-infrared light beam produced due to propagation of the near-infrared light beam through the living organism;
second demodulation means for spectrum-despreading the primary demodulated signal by using the spread code sequence to thereby output a secondary demodulated signal, the spread code sequence being supplied in consideration of the delay of the near-infrared light beam produced due to propagation of the near-infrared light beam through the living organism; and
biological-information-signal output means for outputting a biological information signal representing biological information associated with the metabolism of the living organism by using the secondary demodulated signal output from the second demodulation means.

2. A biological information measuring apparatus according to claim 1, wherein the second frequency coincides with a width of an effective detection band in which the light receiving means of the light detection section can effectively detect the near-infrared light beam having propagated through the living organism.

3. A biological information measuring apparatus according to claim 1, wherein the base-band-signal output means of the light emission section generates and outputs a DC signal.

4. A biological information measuring apparatus according to claim 1, wherein
the base-band-signal output means of the light emission section generates and outputs a generally pulse-shaped signal at an arbitrary frequency equal to or less than half the first frequency; and
the light detection section further comprises third demodulation means for demodulating the second demodulated signal output from the second demodulation means by using the generally pulse-shaped signal supplied in consideration of the delay of the near-infrared light beam produced due to propagation of the near-infrared light beam through the living organism.

5. A biological information measuring apparatus according to claim 4, wherein
the light emission section further comprises an error-correction-code addition means for adding an error correction code to the generally pulse-shaped signal output from the base-band-signal output means; and
the light detection section further comprises error check means for checking consistency of the secondary demodulated signal by using the error correction code contained in the secondary demodulated signal output from the second demodulation means, and interpolation means for restoring the secondary demodulated signal through interpolation when the error check means determines that the secondary demodulated signal contains an error.

6. A biological information measuring apparatus according to claim 1, wherein the spread-code-sequence generation means of the light emission section changes the spreading factor of the spread code sequence in accordance with the intensity of the near-infrared light beam having propagated through the living organism and received by the light receiving means of the light detection section.

7. A biological information measuring apparatus according to claim 6, wherein the spread-code-sequence generation means generates the spread code sequence with an increased spreading factor when the intensity of the near-infrared light beam having propagated through the living organism and received by the light receiving means of the light detection section is low and the SN ratio of the near-infrared light beam is low, and generates the spread code sequence with a decreased spreading factor when the intensity is high and the SN ratio is high.

8. A biological information measuring apparatus according to claim 6, wherein the spread-code-sequence generation means generates, as the spread code sequence, an orthogonal variable spreading factor code which guarantees the orthogonality between spread code sequences which differ in spreading factor.

* * * * *